United States Patent [19]

Nakashima et al.

[11] 4,352,884
[45] Oct. 5, 1982

[54] CARRIER HAVING ACRYLATE COPOLYMER COATING FOR IMMOBILIZATION OF BIOACTIVE MATERIALS

[75] Inventors: Toshihide Nakashima; Masao Tanihara, both of Kurashiki; Koichi Takakura, Okayama, all of Japan

[73] Assignee: Kuraray Co., Ltd, Kurashiki, Japan

[21] Appl. No.: 232,394

[22] Filed: Feb. 9, 1981

[30] Foreign Application Priority Data

Feb. 19, 1980 [JP] Japan .................................. 55-19906

[51] Int. Cl.$^3$ .................. G01N 33/50; G01N 33/54; G01N 31/08; G01N 27/30
[52] U.S. Cl. .................. 435/180; 23/230 B; 23/915; 65/60.3; 204/195 B; 204/195 M; 204/195 P; 422/57; 422/70; 424/12; 427/2; 435/7; 435/181
[58] Field of Search .................. 422/57; 23/230 B; 424/12; 65/60 B; 204/195 B, 195 M, 195 P; 435/180; 427/2

[56] References Cited

U.S. PATENT DOCUMENTS

| | | | |
|---|---|---|---|
| 3,966,580 | 6/1976 | Janata | 204/195 B |
| 4,070,348 | 1/1978 | Kraemer | 435/180 X |
| 4,206,259 | 6/1980 | Rohrbach | 435/180 X |
| 4,242,191 | 12/1980 | Schindler | 204/195 M |
| 4,245,064 | 1/1981 | Drobnik | 435/180 X |

*Primary Examiner*—Sidney Marantz
*Attorney, Agent, or Firm*—Barry Kramer

[57] ABSTRACT

Carriers coated with a copolymer of a hydrophilic acrylate or methacrylate monomer and a copolymerizable unsaturated carboxylic acid or unsaturated amine are provided which are substantially free from nonspecific adsorption of proteins and the like. Due to the side-chain carboxyl or amino groups of the copolymer, these coated carriers are able to immobilize bio-active materials such as antigens, antibodies, complements and enzymes. These carriers, on which bio-active materials can be immobilized, are useful as clinical selective adsorbents, affinity-chromatographic adsorbents, selective electrodes or columns for analysis.

14 Claims, No Drawings

CARRIER HAVING ACRYLATE COPOLYMER COATING FOR IMMOBILIZATION OF BIOACTIVE MATERIALS

BACKGROUND OF THE INVENTION

1. Field of the Invention

This invention relates to carriers for immobilization of physiologically active materials (hereinafter, "bio-active materials"), selective adsorbents, selective electrodes and chromatographic columns comprising said carriers and bio-active materials immobilized thereon. Such carriers for immobilization of a bio-active material immobilize the latter material thereon thereby allowing a specific bio-chemical reaction involving the bio-active material to take place thereon. The term "bio-active material" is used herein to mean any of tissues, cells, enzymes, antigens, antibodies, immune complexes, complements and other serum proteins or polysaccharides or complexes thereof.

2. Description of the Prior Art

It is known that a reaction of bio-active materials on an immobilization carrier enables a quantitative and selective determination of a substance which is reactive in the presence of certain antibodies or antigens either in vivo or in vitro, or a selective removal or withdrawal of certain substances in the course of a chemical reaction, and such reaction on a carrier can be utilized broadly in physiochemical and medical fields. Carriers of this type which have heretofore been commonly employed comprise porous glass or a high polymer substance, such as Sepharose ® (an agarose gel in bead form, manufactured by Pharmacia Fin Chemicals, Sweden) polystyrene bead, and the like, in which functional groups capable of binding with molecules of a bio-active material have been incorporated. The use of such carriers has been limited since they are not specific enough to reject all substances other than the target bio-active material. Thus, when one attempts to introduce functional groups into such a carrier material and cause the target bio-active material to be bound thereto, the unreacted material adsorbed non-specifically thereon is not thoroughly removed but remains on the carrier. Moreover, when one conducts a reaction of such an immobilized bio-active material with a solution (inclusive of body fluids, e.g., blood, plasma, serum, urine) of another material (e.g. the substrate in the case of an enzymatic reaction or the antigen or antibody in an immunological reaction), the heretofore inevitable non-specific adsorption of substances other than desired materials occurs causing a reduction in the specificity of the reaction. Especially when the immobilized bio-active material is used in therapeutic applications, the unreacted material is transferred into the body as a heterologous substance; the blood coagulation factors and platelets are adsorbed to cause clotting or activate the lymphocyte system, with the result that this type of reaction has not been put into clinical practice.

SUMMARY OF THE INVENTION

In accordance with this invention, there is provided a carrier for immobilization of bio-active materials which ensures a minimum of nonspecific adsorption by overcoming the above-mentioned disadvantages. This invention is therefore directed to (1) a carrier for immobilization of bio-active materials which comprises a substrate coated with a copolymer of (i) a hydrophilic acrylate or methacrylate monomer represented by the general formula $CH_2=C(R_1)CO_2R_2OR_3$, wherein $R_1$ is H or methyl; $R_2$ is a divalent alkylene radical of 2 to 3 carbon atoms which may optionally be substituted by lower alkyls, OH, $NH_2$, and the like, or a poly(oxyalkylene) group whose repeating unit is an oxyalkylene group of 2 to 3 carbon atoms with the number of repetitions being not greater than 30; $R_3$ is H or an alkyl group of 1 to 3 carbon atoms, which alkyl group may be further substituted by polar substituent groups such as OH, $NH_2$, and the like, and (ii) a copolymerizable unsaturated carboxylic acid of the general formula $CH_2=C(R_1)CO_2H$, wherein $R_1$ is H or methyl, or (iii) a copolymerizable unsaturated amine of the general formula $CH_2=C(R_1)CO_2R_2NHR_3$, wherein $R_1$ is H or methyl; $R_2$ is a divalent alkylene radical of 2 to 3 carbon atoms; and $R_3$ is H or an alkyl group of 1 to 3 carbon atoms, said copolymerizable component being present in an amount of from about 1 to 50 weight percent based on the total weight of monomers; (2) a selective adsorbent or electrode comprising the above carrier and a bio-active material immobilized thereon, and (3) an analytical column comprising said carrier and a bio-active material immobilized thereon.

DETAILED DESCRIPTION OF THE INVENTION

The hydrophilic acrylate or methacrylate monomer of the general formula $CH_2=C(R_1)CO_2R_2OR_3$ which is employed according to this invention includes, among others, β-hydroxyethyl acrylate, γ-hydroxypropyl acrylate, β-alkoxyethyl acrylate, γ-alkoxypropyl acrylate, aminoalkoxyethyl acrylate, aminoalkoxypropyl acrylate, hydroxyalkoxyethyl acrylate, and the like, as well as the corresponding methacrylates. The unsaturated carboxylic acid of the general formula $CH_2=C(R_1)CO_2H$ is methacrylic acid or acrylic acid.

The unsaturated amine of the general formula $CH_2=C(R_1)CO_2R_2NHR_3$ may, for example, be aminoethyl acrylate, aminopropyl acrylate, monoalkylaminoethyl acrylate, monoalkylaminopropyl acrylate, and the like, as well as the corresponding methacrylates.

The copolymerizing ratio of said unsaturated carboxylic acid or amine can range from 1 to 50 weight percent based on the total weight of monomers and preferably ranges from about 10 to 40 weight percent.

The substrate or base material to be coated with the above copolymer can be one of various materials which is selected according to the intended application but generally speaking, includes inorganic materials such as glass, activated carbon, silica, alumina, and the like, synthetic high polymers such as polystyrene, polyethylene, polyvinyl chloride, nylon, polyester, polymethyl methacrylate, and the like, and naturally occurring high polymers such as cellulose.

These materials are suitably employed in the form of grains, webs, sheets, tubes, electrodes, and the like. Such base materials are desirably used selectively in accordance with the intended applications. For example, when the intended application is a clinical selective adsorbent, the base material is preferably in the form of grains with a particle diameter of 0.05 to 5 millimeters. Glass beads are most desirable in that they are free from the problem of a portion being destroyed by friction in use and fragments thereof finding their way into the blood or being dissolved in the blood and transmitted into the body.

When the intended application is an adsorbent for affinity chromatography or a column for chromatographic analysis, the base material is preferably in the form of grains or a tube of glass or synthetic resin. When the base material is an electrode, the carrier can be used for a quantitative determination of specific substances through reactions involving bio-active materials such as antigens, antibodies, complements, enzymes, and the like. Further, as a particulate base material, a porous material having a large surface area is preferred because it will immobilize a large amount of bio-active material per unit weight.

As examples of the bio-active material immobilized on the carrier according to this invention, there may be mentioned biological tissues, cells, antigens, antibodies, antigen-antibody complexes, complements, enzymes and the like. The antigens include blood proteins such as albumin, immunoglobulins, and the like, nucleic acids such as DNA, RNA, and the like, proteins produced by bacteria such as Protein A, and bacterial extracellular polysaccharides. The antibodies include those various antibodies corresponding to said antigens. The applicable complements include all of $C_1$ to $C_9$ complements, and the receptors include Fc receptor, acetylcholine receptor and various hormone receptors. The enzymes can be acetylcholinesterase, alcohol dehydrogenase, alkaline phosphatase, aminopeptidase, α-amylase, aspartate aminotransferase, catalase, cellulase, cholesterol esterase, α-chymotrypsin, deoxyribonuclease, glucose oxidase, L-glutaminate decarboxylase, lactate dehydrogenase, lipase, lysozyme, nuclease, pepsin, peroxidase, protease, ribonuclease, ligase, tryspin, urease, and the like.

The carrier for immobilization of bio-active materials in accordance with this invention can be produced in the following manner. First, a copolymer dope is prepared by the conventional solution polymerization method using the above-mentioned hydrophilic acrylate or methacrylate monomer and the above-mentioned copolymerizable unsaturated carboxylic acid or unsaturated amine as starting materials and the surface of the above-mentioned base material is coated with said copolymer dope by a conventional coating or deposition procedure such as spraying, dipping, phase-separation or the like. The above copolymer dope may also be prepared with the addition of a small amount of an epoxy group-containing monomer such as glycidyl acrylate, glycidyl methacrylate or the like as a copolymerizable component or such a copolymeric component may be added to the above-mentioned copolymer dope. In both cases, a cross-linking treatment after the coating process will provide for the prevention of elution from the coating layer.

The base material coated in the above manner has been covered with a hydrophilic surface carrying carboxyl or amino groups and bio-active materials can be immobilized either directly on these carboxyl or amino groups or through other groups of comparatively low molecular weight. In the former case of direct coupling, the amino and carboxyl groups of said carrier and bio-active materials can be combined by condensation in the presence of a condensing agent such as dicyclohexylcarbodiimide (DCC), 1-ethyl-3-(3-dimethylaminopropyl) carbodiimide hydrochloride (EDC) and the like. Alternatively, each carboxyl group of the carrier can be transformed into an active N-hydroxysuccinimide ester and the bio-active material then can be introduced by way of substitution. The active ester mentioned above is comparatively stable and is, therefore, storable. In the case of indirect coupling, ε-aminocaproic acid can be attached to the above-mentioned carboxyl group and the bio-active material can be immobilized by the terminal carboxylic acid employing the above-mentioned active ester method. As an alternative, diaminoheptane can be combined with the carboxyl group and, then, the terminal amino group and a bio-active material can be coupled by means of glutaraldehyde or a carbodiimide. Alternatively, the amino groups of the carrier can be coupled to the bio-active material by means of glutaraldehyde.

Following the immobilization of the bio-active material, unreacted materials can be easily removed by washing with a buffer solution and the removal can be confirmed from the ultraviolet spectrum or a color reaction of the washings.

A primary use for the carrier for immobilization of bio-active materials which is thus obtained, is as a clinical or therapeutic selective adsorbent. The bio-active materials in such application include antigens, antibodies, enzymes, complements, and the like. Of course, a material suited for the disease to be treated is selected. For example, the causative agents of autoimmune diseases such as autoimmune hemolytic anemia, glomerulonephritis, chronic rheumatoid arthritis, systemic lupus erythematosus, and the like, are auto-antibodies or immune complexes, and these must be removed from the circulatory system. To eliminate such auto-antibodies and immune complexes, Protein A which is produced by certain strains of *Staphylococcus aureus*, Fc receptors existing on the cell walls of lymphocytes and platelets, complement $C_1$ component, anti-immunoglobulin antibodies, and the like which specifically bind the above-mentioned causative agents are immobilized on the carrier and used as therapeutic selective adsorbents. In patients with renal failure, because urea in the blood is not metabolized but accumulates, a carrier on which urease, the enzyme capable of decomposing urea, has been immobilized can be employed as a therapeutic selective adsorbent. In cancer patients, it has been demonstrated that several immunosuppresive factors against tumor cells exist in the blood and because these immunosuppresive factors occur in the antibody fraction and the antigen protein fraction with a molecular weight range of 10,000 to 100,000, the antibodies to these antigens, Protein A, cell wall Fc receptors, and anti-immunoglobulin antibodies are immobilized on the carrier and used as therapeutic selective adsorbents.

If in such a therapeutic adsorbent, a nonspecific adsorption of proteins takes place, the immobilization of bio-active materials will accompany not only those covalently immobilized, but those physically adsorbed, and when the adsorbent is later contacted with blood or plasma, for instance, the physically adsorbed substances are desorbed and translocated into the body where they act as antigens to induce immunologic reactions. The repeated use of such an adsorbent is dangerous because it could cause an anaphilactic shock. In contrast, the therapeutic selective adsorbent of this invention presents no such problem because the nonspecific adsorption of proteins is precluded by the copolymer covering the base material. Moreover, with the therapeutic selective adsorbent of this invention, adsorption occurs with a very high selectivity, and, therefore, simultaneous adsorption of useful components of blood or plasma is successfully precluded.

Another use for the immobilization carrier of this invention is as an affinity-chromatographic adsorbent which is employed for the separation and purification of proteins, nucleic acids, polysaccharides, hormones, vitamins, cells and the like. In these applications, the bio-active material to be immobilized is selected in accordance with the substance to be purified. For example, when it is contemplated to separate T-cells from B-cells or vice versa, lymphocytes are first collected from the blood by a conventional procedure such as density-gradient centrifugation. Then, a suspension of the lymphocyte fraction is contacted with an affinity-chromatographic adsorbent carrying anti-immunoglobulin antibodies immobilized on the base material, whereupon B-cells are selectively adsorbed on the adsorbent, with the T-cells emerging from the adsorbent. The adsorbed B-cells are desorbed with an immunoglobulin solution. Further, if an antiserum or a solution containing a hormone or a vitamin is contacted with an affinity-chromotagraphic adsorbent of this invention carrying albumin or immunoglobulin or an antibody or receptor of the hormone or vitamin is immobilized thereon, the anti-albumin antibody or anti-immunoglobulin antibody in the antiserum or the hormone or vitamin is selectively adsorbed on the adsorbent. The desired substance can then be eluted with a buffer solution other than physiological pH, a concentrated salt solution or a surfactant solution. When nonspecific adsorption takes place on the affinity-chromatographic adsorbent, substances other than the desired substance are also adsorbed and these substances are also eluted together with the desired substance to jeopardize the purification procedure. However, the affinity-chromatographic adsorbent according to this invention permits a high degree of purification because of the absence of nonspecific adsorption and, hence, of contamination of the eluate with impurities.

A further use for the immobilization carrier of this invention is as a selective electrode comprising a metal electrode such as an electrode of platinum black, copper or the like, a pH electrode made of glass, a FET sensor made of silicon nitride or the like as the base material and an enzyme, antigen, antibody, complement or the like immobilized on the surface of the base material. Thus, as the bio-active material immobilized on the surface of such an electrode reacts with the substance to be detected, an electric current is generated in the electrode or a change of electric potential takes place around the electrode, thus allowing the specific substance reactive to said bio-active material to be selectively detected. For example, with a selective electrode produced by immobilizing urease on the surface of a glass pH electrode, the titer of urea in a specimen can be detected because the urease converts the urea to ammonia which excites the pH electrode. With an electrode produced by immobilizing an antigen such as DNA or albumin or an antibody such as an anti-immunoglobulin antibody on the surface of a FET pH sensor, the antibody such as anti-DNA antibody, anti-albumin antibody or the like or the antigen such as immunoglobulin can be selectively detected. In nonspecific adsorption of proteins and the like takes place on the electrode, there will occur a drift or noise because changes in potential or current will also be induced by the adsorption of substances other than the target material on the electrode surface. The drift or noise interferes with stable and reliable determinations. Because of the absence of nonspecific adsorption of proteins, and the like, the selective electrode according to this invention ensures stable and reproducible determinations.

A still further use for the immobilization carrier of this invention is in a column for analysis, especially one capable of continuous analysis of a plurality of samples in a short period of time. The column may be a column of glass, organic polymer or metal packed with grains or beads of glass or organic polymer or such a column whose inside wall serves as a carrier for a bio-active material. The bio-active materials used in this application are selected from among antigens, antibodies, complements and enzymes in accordance with the intended application. By way of example, a column for analysis is prepared by packing one half of the space toward the inlet of a glass column with the present carrier comprising glass beads carrying glucoseoxidase as immobilized thereon and the remaining half space with a similar carrier carrying peroxidase, and a sample containing glucose is passed through the column. The glucoseoxidase decomposes the glucose to yield gluconic acid and hydrogen peroxide. Then peroxidase reacts with the hydrogen peroxide quantitatively and oxidatively couples phenol and 4-aminoantipyrine to yield a red dye. The absorbance at 505 nm is then measured with the flow cell of a spectrophotometer to estimate the concentration of glucose in the sample. If the antibody to α-fetoprotein found in the blood of cancer patients is immobilized in the analytical column of this invention and a plasma or serum sample is passed through the column, the α-fetoprotein alone is trapped in the column. If, after the column is washed, the covalent conjugate of the antibody to α-fetoprotein with peroxidase is introduced into the column, the quantity of peroxidase corresponding to the trapped amount of α-fetoprotein is trapped in the column. The column is washed to remove the untrapped peroxidase and a color reagent mixture of phenol and 4-aminoantipyrine is passed through the column, whereupon a red dye is formed in an amount corresponding to the amount of peroxidase. The absorbance at 505 nm is then measured with a spectrophotometer to estimate the concentration of α-fetoprotein in the sample. If, after this determination, the adsorbent is washed with a surfactant solution or a concentrated salt solution, the trapped α-fetoprotein, oxidase, and the like, are desorbed and the column is readied for analysis of the next sample. If, however, nonspecific adsorption of proteins and the like takes place in the analytical column, the immobilized bio-active material will be covered up with the adsorbed matters so that it will not be sufficiently reactive, or reactions of adsorbed proteins and the like will interfere with the desired reaction of the sample or make color assays difficult. These phenomena lead to inaccurate analyses and shorten the useful life of the analytical column. However, the analytical column according to this invention is free from nonspecific adsorption of proteins, and the like, and, therefore, permits stable analyses over many hours.

The following examples are further illustrative but by no means limitative of this invention.

EXAMPLE 1

Amberlite XAD-7, the porous methacrylate adsorbent of Rohm and Haas Co., Ltd., was immersed in an 0.5% aqueous ethanol solution of a copolymer of 20 weight percent methacrylic acid, 79.5 weight percent hydroxyethyl methacrylate and 0.5 weight percent glycidyl methacrylate and, after drying, a curing reaction was carried out at 120° C. for 2 hours. As will be seen from Tables 1 and 2, whereas uncoated XAD-7 adsorbed appreciable amounts of bovine serum albumin and bovine serum γ-globulin, the above-coated XAD-7 did not substantially adsorb the two proteins.

TABLE 1

Adsorption of bovine serum albumin, 37° C., 10 ml of phosphate buffered saline/1 g dry XAD-7

| | Concentration of albumin in supernatant (g/dl) | |
|---|---|---|
| | Initial Concentration | After 2 hrs. |
| Uncoated XAD-7 | 1.5 | 0.5 |
| Coated XAD-7 | 1.8 | 1.7 |

TABLE 2

Adsorption of bovine γ-globulin (Same conditions as Table 1)

| | Concentration of γ-globulin in supernatant (g/dl) | |
|---|---|---|
| | Initial Concentration | After 2 hrs. |
| Uncoated XAD-7 | 1.5 | 0.9 |
| Coated XAD-7 | 1.5 | 1.5 |

The coated XAD-7 is reacted with N-hydroxysuccinimide in dioxane to produce the active ester and urease is reacted in phosphate buffer for immobilization. The urease was immobilized without losing its enzymatic activity and the product showed the urease activity shown in Table 3.

The BET surface area of uncoated XAD-7 was 480 m$^2$/g and that of the coated XAD-7 was 410 m$^2$/g, which represented only a small reduction in area.

TABLE 3

UREASE ACTIVITY, 37° C.

| | Concentration of Urea (mg/dl) | |
|---|---|---|
| | Initial Concentration | After 2 hrs. |
| XAD-7 (Example 1) | 50 | 14 |
| CPG-10-700 (Example 2) | 85 | 24 |

EXAMPLE 2

CPG-10-700, the porous glass of Electro-Nucleonics, Inc., was treated with 3-aminopropyltriethoxysilane and, then, coated with the same copolymer as that used in Example 1. As shown in Tables 4 and 5, whereas uncoated CPG-10-700 adsorbed appreciable amounts of bovine serum albumin and bovine γ-globulin, the coated CPG did not substantially adsorb these proteins.

When urease was immobilized on the carrier as in Example 1, there was no substantial loss of urease activity as shown in Table 3.

TABLE 4

Adsorption of bovine serum albumin (Same conditions as Table 1)

| | Concentration of albumin in supernatant (g/dl) | |
|---|---|---|
| | Initial Concentration | After 2 hrs. |
| Uncoated CPG-10-700 | 1.8 | 1.0 |
| Coated CPT-10-700 | 1.8 | 2.0 |

The BET surface area and pore volume of uncoated CPG-10-700 was 37 m$^2$/g and 1.25 cm$^3$g, respectively, and the corresponding values of the coated CPG-10-700 were 32 m$^2$/g and 1.11 cm$^3$/g. Thus, the decrease of porosity was negligible.

EXAMPLE 3

Glass beads from 0.2 to 0.6 mm in diameter were immersed in 50% hydrofluoric acid at room temperature for 1 hour and, then, heat-treated in a 10 M solution of NaOH at 80° C. for 1 hour. The glass beads were then sprayed with an 0.5% ethanol solution of a copolymer of 79 weight percent of hydroxyethyl methacrylate, 20 weight percent of methacrylic acid and 1 weight percent of glycidyl methacrylate. The weight ratio of the copolymer was about 0.5 weight percent with respect to the glass beads. The resultant carrier for immobilization of bio-active materials did not absorb bovine serum albumin or/and γ-globulin at all.

Twenty (20) grams of this carrier was activated in the same manner as Example 1 and 50 mg of bovine serum albumin was immobilized thereon. A column was packed with the above carrier and 20 ml of a canine ACD plasma sample containing about 6.9 mg of anti-bovine serum albumin antibody (Miles Laboratories, Inc.) was circulated at the flow rate of 6.2 ml/min. Whereas the plasma prior to circulation formed precipitates with 20 mg/dl phosphate buffered saline solutions of bovine serum albumin, the plasma after 2 hours of circulation did not form precipitates any longer. Thus, with the carrier having bovine serum albumin immobilized thereon according to this invention, the anti-bovine serum albumin antibody in canine plasma could be successfully adsorbed and removed.

EXAMPLE 4

A column was packed with 15 g of a carrier on which about 2.3 mg of anti-bovine serum albumin antibody had been immobilized in the same manner as Example 3, and 10 ml of phosphate buffered saline containing 2.2 mg of bovine serum albumin was circulated through the column.

Whereas a 4-fold dilution of the solution prior to circulation formed precipitates with a 46 mg/dl aqueous solution of anti-bovine serum albumin antibody, a 4-fold dilution of the solution after one hour of circulation did not form precipitates any longer. Thus, with the carrier having anti-bovine serum albumin antibody according to this invention, the bovine serum albumin in the solution could be successfully adsorbed and removed.

EXAMPLE 5

In the same manner as Example 3, anti-bovine serum albumin antibody (rabbit, Miles Laboratories, Inc.,) was coupled to Amberlite XAD-4, the styrene porous resin of Rohm and Haas Co., Ltd., to prepare an adsorbent for affinity chromatography. Fifteen (15) grams of the above adsorbent was filled into a polypropylene column equipped with a support net on either end. After the column was washed thoroughly with phosphate buffered saline (PBS pH 7.4), 100 ml of a solution containing 5 mg/dl each of bovine serum albumin (Sigma Chemicals, Fraction V) and bovine serum γ-globulin (Sigma Chemicals, Fraction II) was passed through the column. The column was washed with PBS and, then, 100 ml of a 3 M potassium thiocyanate/PBS solution was passed. The eluate was dialyzed against PBS at 4° C. for 24 hours. The total protein concentration of this solution was measured by the biurett method and the albumin concentration by the bromocresolgreen method to determine the purity and percent recovery of albumin.

The results were: total protein 2.0 gm, albumin 2.0 mg, purity of albumin 100%, percent recovery of albumin 40%.

EXAMPLE 6

A glass pH electrode (Hitachi-Horiba) was immersed in a 5% ethanol solution of the copolymer of 79 weight percent hydroxyethyl methacrylate, 20 weight percent methacrylic acid and 1 weight percent glycidyl methacrylate, followed by drying in a hot air current. The above procedure was repeated for a total of 3 times. Then, in phosphate buffer, urease was immobilized on the coated carrier in the presence of 1-ethyl-3-(3-dimethylaminopropyl) carbodiimide hydrochloride to prepare an electrode for detection of urea. This electrode was connected to a Hitachi-Horiba F-5 pH meter to detect the difference between the urea solution and urea-free solution. It was found that the urea solution showed a pH increase substantially proportional to the concentration of urea. This means that this electrode permits a continuous assay of urea.

EXAMPLE 7

One gram of the coated Amberlite XAD-7 prepared in Example 1 was treated with glucoseoxidase (Miles Laboratories, Inc., activity 25 U/mg) in phosphate buffer (pH 7.4), while one gram of the same Amberlite XAD-7 was treated with peroxisase (Miles Laboratories, horse-radish, activity 100 U/mg). These two immobilized enzymes were serially filled into a glass column with an inside diameter of 6 mm to prepare a column for analysis. The exit end of the column near the peroxidase was connected to the flow-cell of a Hitachi 220 spectrophotometer. As a solution containing glucose was passed from the inlet end of the column (near the glucoseoxidase), the absorbance at 505 nm was increased. This increase of absorbance was proportional to the glucose concentration of the solution. It was found, therefore, that this column for analysis was useful for a quantitative estimation of glucose.

What is claimed is:

1. A carrier for immobilization of bio-active materials which comprises a base material coated with a copolymer of (i) a hydrophilic acrylate or methacrylate monomer of the general formula $CH_2=C(R_1)CO_2R_2OR_3$, wherein $R_1$ is H or methyl; $R_2$ is a substituted or unsubstituted divalent alkylene radical of 2 to 3 carbon atoms or a poly(oxyalkylene) radical; $R_3$ is H or an alkyl radical of 1 to 3 carbon atoms, which alkyl radical can be further substituted by polar substituent groups and (ii) a copolymerizable unsaturated carboxylic acid of the general formula $CH_2=C(R_1)CO_2H$, wherein $R_1$ is H or methyl or (iii) a copolymerizable unsaturated amine of the general formula $CH_2=C(R_1)CO_2R_2NHR_3$, wherein $R_1$ is H or methyl; $R_2$ is a divalent alkylene radical of 2 or 3 carbon atoms; and $R_3$ is H or an alkyl radical of 1 to 3 carbon atoms, said copolymerizable component being present in amount of from about 1 to 50 weight percent based on the total weight of monomers.

2. A carrier for immobilization of bio-active materials as claimed in claim 1 wherein the base material is a member selected from the group consisting of glass, activated carbon, silica, alumina and high molecular weight organic compounds and said base material is employed in the form of grains, beads, webs, sheets or tubes.

3. A carrier for immobilization of bio-active materials as claimed in claim 2 wherein the base material is a porous or nonporous glass with a particle diameter from 0.05 to 5 millimeters.

4. A carrier for immobilization of bio-active materials as claimed in claim 1 wherein the copolymer additionally contains a sufficient amount of an epoxy-containing monomer to effect cross-linking of the copolymer coating upon subsequent curing.

5. A carrier for immobilization of bio-active materials as claimed in claim 1 wherein the copolymerizable component is present in the copolymer in amounts of from about 10 to 40 weight percent.

6. A clinical selective adsorbent comprising a bio-active material immobilized on a base material coated with a copolymer as claimed in claim 1.

7. A clinical selective adsorbent as claimed in claim 6 wherein the base material is a porous or nonporous glass with a particle diameter of 0.05 to 5 millimeters.

8. A clinical selective adsorbent as claimed in claim 6 wherein the bio-active material is a member selected from the group consisting of antigens, antibodies, complements, receptors and enzymes.

9. A clinical selective adsorbent as claimed in claim 6 wherein the bio-active material is a member selected from the group consisting of protein A, cell wall Fc receptor, complement Cl component, anti-immunoglobulin antibody and immunoglobulin.

10. An affinity chromatographic adsorbent comprising an antigen, antibody, complement or enzyme immobilized on a particulate or tubular base material coated with a copolymer as in claim 1.

11. An affinity chromatographic adsorbent as claimed in claim 10 wherein said particulate material comprises beads of glass or high molecular weight organic compounds having a particle size of 0.05 to 5 millimeters.

12. An affinity chromatographic adsorbent as claimed in claim 10 wherein said tubular material is a tube of glass or an organic polymer.

13. A selective electrode coated on the surface thereof with a copolymer as claimed in claim 1 and carrying an antigen, antibody, complement or enzyme immobilized on the surface so coated.

14. A column for analysis, a portion or the whole of which, comprises a surface formed of beads or a tube of glass or an organic polymer coated with a copolymer as claimed in claim 1 and carrying an antigen, antibody, complement or enzyme immobilized on the surface so coated.

* * * * *